US012544080B2

(12) United States Patent
Atkin et al.

(10) Patent No.: US 12,544,080 B2
(45) Date of Patent: Feb. 10, 2026

(54) INDEXABLE FEMORAL NECK RESECTION GUIDE

(71) Applicant: DEPUY IRELAND UNLIMITED COMPANY, Ringaskiddy (IE)

(72) Inventors: Jamie Atkin, Leeds (GB); Sarah Bushell, Leeds (GB); Stephen Robinson, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 619 days.

(21) Appl. No.: 17/602,087

(22) PCT Filed: Apr. 16, 2020

(86) PCT No.: PCT/EP2020/060789

§ 371 (c)(1),
(2) Date: Oct. 7, 2021

(87) PCT Pub. No.: WO2020/212539

PCT Pub. Date: Oct. 22, 2020

(65) Prior Publication Data

US 2022/0125440 A1 Apr. 28, 2022

(30) Foreign Application Priority Data

Apr. 17, 2019 (GB) ..................................... 1905459

(51) Int. Cl.
*A61B 17/15* (2006.01)
*A61B 17/00* (2006.01)

(52) U.S. Cl.
CPC .... *A61B 17/15* (2013.01); *A61B 2017/00725* (2013.01)

(58) Field of Classification Search
CPC ..... A61B 17/15; A61B 17/151; A61B 17/152; A61B 17/154; A61B 17/155; A61B 2017/00725
See application file for complete search history.

(56) References Cited

U.S. PATENT DOCUMENTS 3,810,312 A 5/1974 Carson
3,889,558 A 6/1975 Duncan
(Continued)

FOREIGN PATENT DOCUMENTS

CN 1193899 A 9/1998
CN 102048599 A 5/2011
(Continued)

OTHER PUBLICATIONS

D.H. Lucase MD, R.D. Scott, MD, The Ranawat Sign, A Specific Maneuver to Assess Component Positioning in Total Hip Arthroplasty. Joumal of Orthopaedic Techniques, vol. 2, No. 2 Jun. 1994, pp. 59-61.

(Continued)

*Primary Examiner* — Tracy L Kamikawa
(74) *Attorney, Agent, or Firm* — Barnes & Thornburg LLP

(57) ABSTRACT

The invention relates to a surgical device for performing a controlled resection of the neck of a femur during a hip replacement procedure. The surgical device comprises a template comprising an aperture dimensioned for receiving a femoral head of the femur, and a frame comprising a resection guide for indicating a resection plane on the femoral neck. The femoral neck has a femoral neck axis. The frame is slidably connected to the template for positioning of the resection guide along the femoral neck axis while the template is mounted on the femoral head.

11 Claims, 7 Drawing Sheets

(56) References Cited

U.S. PATENT DOCUMENTS 3,987,499 A 10/1976 Scharbach et al.
4,305,394 A 12/1981 Bertuch, Jr.
4,306,550 A 12/1981 Forte
4,552,136 A 11/1985 Kenna
4,587,964 A 5/1986 Walker et al.
4,601,289 A 7/1986 Chiarizzio et al.
4,693,724 A 9/1987 Rhenter et al.
4,959,066 A 9/1990 Dunn et al.
4,962,155 A 10/1990 Fujita Yamaguchi
4,963,155 A 10/1990 Lazzeri et al.
5,002,578 A 3/1991 Luman
5,002,581 A 3/1991 Paxson et al.
5,041,118 A 8/1991 Wasilewski
5,057,112 A 10/1991 Sherman et al.
5,169,401 A 12/1992 Lester et al.
5,190,550 A 3/1993 Miller et al.
5,261,915 A 11/1993 Durlacher et al.
5,336,268 A 8/1994 Rispeter
5,342,363 A 8/1994 Richelsoph
5,352,231 A 10/1994 Brumfield et al.
5,409,492 A 4/1995 Jones et al.
5,480,451 A 1/1996 Grundei
5,540,687 A 7/1996 Fairley et al.
5,569,263 A 10/1996 Hein
5,645,607 A 7/1997 Hickey
5,653,764 A 8/1997 Murphy
5,653,765 A 8/1997 Mctighe et al.
5,766,261 A 6/1998 Neal et al.
5,858,020 A 1/1999 Johnson et al.
5,876,459 A 3/1999 Powell
5,888,208 A 3/1999 Ro
5,906,644 A 5/1999 Powell
5,938,701 A 8/1999 Hiernard et al.
5,951,606 A 9/1999 Burke
6,042,611 A 3/2000 Noiles
6,048,365 A 4/2000 Burrows et al.
6,080,162 A 6/2000 Dye et al.
6,090,146 A 7/2000 Rozow, III et al.
6,110,179 A 8/2000 Flivik et al.
6,149,687 A 11/2000 Gray, Jr. et al.
6,165,177 A 12/2000 Wilson et al.
6,193,759 B1 2/2001 Ro et al.
6,238,435 B1 5/2001 Meulink et al.
6,258,097 B1 7/2001 Cook et al.
6,306,174 B1 10/2001 Gie et al.
6,330,845 B1 12/2001 Meulink
6,447,518 B1 9/2002 Krause
6,464,728 B1 10/2002 Murray
6,491,696 B1 12/2002 Kunkel
6,503,255 B1 * 1/2003 Albrektsson ........... A61B 17/15 606/89
6,679,917 B2 1/2004 Ek
6,702,854 B1 3/2004 Cheal et al.
6,706,072 B2 3/2004 Dwyer
6,743,235 B2 6/2004 Subba Rao
6,883,217 B2 4/2005 Barrette et al.
6,905,515 B1 6/2005 Gilbertson
7,022,141 B2 4/2006 Dwyer et al.
7,066,042 B2 6/2006 Andrews et al.
7,135,044 B2 11/2006 Bassik
7,188,556 B1 3/2007 Rinner
7,297,166 B2 11/2007 Dwyer et al.
7,363,838 B2 4/2008 Abdelgany
7,572,297 B2 8/2009 Cheal et al.
7,582,092 B2 9/2009 Jones et al.
7,585,329 B2 9/2009 Mccleary et al.
7,601,155 B2 * 10/2009 Petersen .............. A61B 17/175 606/85
7,641,698 B1 1/2010 Gibbs
7,799,086 B2 9/2010 Justin et al.
7,981,161 B2 7/2011 Choi
8,048,167 B2 11/2011 Dietz
8,449,619 B2 5/2013 Metcalfe
8,506,642 B1 8/2013 Lyren
8,562,690 B1 10/2013 Dickerson
8,696,758 B2 4/2014 Hood et al.
9,603,720 B2 * 3/2017 Kelley ................. A61B 17/155
9,668,746 B2 * 6/2017 Lee ........................ A61B 17/15
11,344,437 B2 5/2022 Bailey
11,369,492 B2 6/2022 Horne et al.
11,826,267 B2 11/2023 Bushell et al.
2002/0038148 A1 3/2002 Fernandez et al.
2002/0058999 A1 5/2002 Dwyer et al.
2003/0074080 A1 4/2003 Murray
2003/0149487 A1 8/2003 Doubler et al.
2004/0004186 A1 1/2004 Jiyan
2004/0054373 A1 3/2004 Serra et al.
2004/0064186 A1 4/2004 Mccleary et al.
2004/0073315 A1 4/2004 Justin et al.
2004/0116933 A1 6/2004 White
2004/0122437 A1 6/2004 Dwyer et al.
2004/0122439 A1 6/2004 Dwyer et al.
2004/0122440 A1 6/2004 Daniels
2004/0122525 A1 6/2004 Daniels et al.
2004/0172139 A1 9/2004 Dwyer et al.
2004/0236341 A1 11/2004 Petersen
2004/0267267 A1 12/2004 Daniels et al.
2004/0267372 A1 12/2004 Vanasse et al.
2004/0267373 A1 12/2004 Dwyer et al.
2005/0033444 A1 2/2005 Jones et al.
2005/0107799 A1 5/2005 Graf
2005/0143828 A1 6/2005 Collins
2005/0203634 A1 9/2005 Bassik et al.
2005/0245934 A1 11/2005 Tuke
2006/0027027 A1 2/2006 Serra et al.
2006/0217737 A1 9/2006 Iversen
2006/0241625 A1 10/2006 Metcalfe et al.
2006/0260440 A1 11/2006 Abdelgany
2007/0005144 A1 1/2007 Leisinger et al.
2007/0050039 A1 3/2007 Dietz
2007/0100464 A1 5/2007 Meulink
2007/0123908 A1 5/2007 Jones et al.
2007/0219641 A1 9/2007 Dorr et al.
2007/0233132 A1 10/2007 Valla
2007/0244566 A1 10/2007 Daniels et al.
2008/0091212 A1 4/2008 Dwyer et al.
2008/0133023 A1 6/2008 Schlotterback et al.
2008/0262626 A1 10/2008 Raugel
2009/0048682 A1 2/2009 Choi
2009/0054993 A1 2/2009 Le Bon et al.
2009/0112216 A1 4/2009 Leisinger
2009/0112218 A1 4/2009 Mccleary et al.
2009/0187251 A1 7/2009 Justin et al.
2009/0307887 A1 12/2009 Jones et al.
2010/0023014 A1 1/2010 Romagnoli et al.
2010/0100193 A1 4/2010 White
2010/0241239 A1 9/2010 Smith
2010/0249943 A1 9/2010 Bergin et al.
2011/0009976 A1 1/2011 Cruchet
2011/0035021 A1 2/2011 Bergin et al.
2011/0054628 A1 3/2011 Banks et al.
2011/0125285 A1 5/2011 Ragbir
2011/0224798 A1 9/2011 Caillouette et al.
2011/0302760 A1 12/2011 Leisinger et al.
2012/0010722 A1 1/2012 Walter et al.
2012/0053698 A1 3/2012 Huff et al.
2012/0259338 A1 10/2012 Carr et al.
2012/0259423 A1 10/2012 Carr
2012/0290099 A1 11/2012 Gibson et al.
2013/0079888 A1 3/2013 Meulink
2013/0144397 A1 6/2013 Smith
2013/0158674 A1 6/2013 Chow
2013/0261762 A1 10/2013 Kennedy
2014/0012392 A1 1/2014 Walter et al.
2014/0276850 A1 9/2014 Chaney et al.
2014/0276866 A1 9/2014 Endsley
2015/0018961 A1 1/2015 Huddle et al.
2015/0039093 A1 2/2015 Mctighe et al.
2015/0083116 A1 3/2015 Zhu
2016/0030200 A1 2/2016 Hunt et al.
2016/0175109 A1 6/2016 Reu et al.
2016/0235417 A1 8/2016 Duncan et al.
2016/0302803 A1 10/2016 Macke et al.
2018/0116822 A1 5/2018 Grobler

(56) References Cited

U.S. PATENT DOCUMENTS

| | | | |
|---|---|---|---|
| 2018/0303495 | A1 | 10/2018 | Hirt et al. |
| 2019/0099191 | A1 | 4/2019 | Huff et al. |
| 2019/0247063 | A1 | 8/2019 | Huff et al. |
| 2019/0336145 | A1 | 11/2019 | Bader et al. |
| 2020/0222208 | A1 | 7/2020 | Bushell et al. |
| 2020/0268527 | A1 | 8/2020 | Maniar et al. |
| 2020/0276029 | A1 | 9/2020 | Bailey |
| 2020/0352742 | A1 | 11/2020 | Horne et al. |
| 2021/0093332 | A1 | 4/2021 | Walker |
| 2021/0228219 | A1 | 7/2021 | Clements et al. |
| 2021/0353433 | A1 | 11/2021 | Huff et al. |
| 2022/0031476 | A1 | 2/2022 | Ait Si Selmi et al. |
| 2022/0218489 | A1 | 7/2022 | Anderson et al. |
| 2023/0293315 | A1 | 9/2023 | Shimeno |

FOREIGN PATENT DOCUMENTS

| | | | |
|---|---|---|---|
| CN | 106264797 | A | 1/2017 |
| DE | 20114835 | U1 | 1/2002 |
| DE | 202007009646 | U1 | 10/2007 |
| DE | 102006031573 | A1 | 1/2008 |
| DE | 102007032014 83 | | 10/2008 |
| EP | 1000595 | A1 | 5/2000 |
| EP | 1435223 | A1 | 1/2004 |
| EP | 1522284 | A2 | 4/2005 |
| EP | 1950396 | A1 | 7/2008 |
| EP | 2027833 | A1 | 2/2009 |
| EP | 2055273 | A1 | 5/2009 |
| EP | 2057969 | A2 | 5/2009 |
| FR | 2574283 | A1 | 6/1986 |
| FR | 2796267 | A1 | 1/2001 |
| FR | 2832624 | A1 | 5/2003 |
| FR | 2865927 | A1 | 8/2005 |
| FR | 2889446 | A1 | 2/2007 |
| FR | 2926212 | A1 | 7/2009 |
| GB | 806441 | A | 12/1958 |
| GB | 2583537 | A | 11/2020 |
| JP | 2012165889 | A | 9/2012 |
| JP | 2013094331 | A | 5/2013 |
| JP | 5859810 | B2 | 2/2016 |
| WO | WO1992003993 | A1 | 3/1992 |
| WO | 1996/36284 | A1 | 11/1996 |
| WO | 9730661 | A1 | 8/1997 |
| WO | WO 1997030661 | A1 | 8/1997 |
| WO | 2002/26145 | A1 | 4/2002 |
| WO | WO1996036284 | A1 | 4/2002 |
| WO | WO2002026145 | A1 | 4/2002 |
| WO | 2007098549 | A1 | 9/2007 |
| WO | 2008069800 | A1 | 6/2008 |
| WO | 2009111459 | A2 | 9/2009 |
| WO | WO2009106866 | A1 | 9/2009 |
| WO | WO2009108683 | A1 | 9/2009 |
| WO | 2012030409 | A1 | 3/2012 |
| WO | 2012034771 | A1 | 3/2012 |
| WO | WO2012035294 | A2 | 3/2012 |
| WO | 2012138824 | A2 | 10/2012 |
| WO | WO2014140636 | A1 | 9/2014 |
| WO | WO2014140639 | | 9/2014 |
| WO | 2018189128 | A1 | 10/2018 |
| WO | 2019068428 | A1 | 4/2019 |

OTHER PUBLICATIONS

GB Search Report for Corresponding GB Patent Application No. GB1905459.2, Dated Oct. 1, 2019, 1 Page.

PCT/EP2020/060789—International Search Report Dated Jul. 7, 2020.

The Ranawat Sign a Specific Maneuver to Assess Component Positioning in Total Hip Arthroplasty, Lucas, David H., and Scott, Richard D., Journal of Orthopaedic Techniques, vol. 2, No. 2, Jun. 1994.

Engage Modular Revision Hip System: Surgical Technique, 2007, DePuy Orthopaedics, Inc, 19 pages.

* cited by examiner

INDEXABLE FEMORAL NECK RESECTION GUIDE

CROSS-REFERENCE TO RELATED APPLICATIONS

This application is a National Stage Application filed Under 35 U.S.C. § 371 of International Application No. PCT/EP2020/060789 filed Apr. 16, 2020, which claims priority to GB1905459.2 filed Apr. 17, 2019, which are hereby incorporated by reference in their entireties.

FIELD OF THE INVENTION

This invention relates to a surgical device and method for performing a controlled resection of the neck of a femur during a hip replacement procedure.

BACKGROUND OF THE INVENTION

Hip replacement is a surgical procedure in which the hip joint is replaced by a prosthetic implant. In total hip replacement surgery, a patient's natural hip is replaced by an acetabular cup component that replaces the acetabular socket and a femoral component that replaces the femoral head.

During such a surgical procedure, a diseased portion of the femur is excised, usually by removing the femoral head prior to milling of the calcar face. A prosthetic femoral component and a prosthetic femoral head replace the natural structures that are surgically removed. The positioning of the femoral component of the prosthesis is important to ensure proper fit and smooth rotation of the femoral head within its socket (i.e., the acetabular shell).

If the surgeon removes too much of the femur at the resection stage, joint tension will have to be manipulated during later stages of the surgical procedure. This can be achieved by increasing head offset or by switching to a high offset neck trial. Both of these approaches would deviate from the optimal surgical plan, potentially increasing the risk of poor post-surgery biomechanics and patient outcome.

Not removing enough bone can make it harder to mill the calcar face effectively, increase bone fragments in the wound space and reduce the performance and life of the calcar mill instrument. Additionally, this leads to inefficiency in the surgical process, associated costs and a reduction in the free space within the wound cavity.

When performing joint reconstruction, such as hip replacement surgery, it is important that the pre-surgical geometry of the bone structure is replicated in the post-surgical structure. It is important to maintain the natural joint biomechanics, ensuring proper joint and soft tissue balancing. If this is not achieved, the result can be higher joint forces, and overall joint instability.

It is therefore necessary to ensure that orthopedic implant structures are properly placed within a patient. In the case of hip joint prostheses, it is important that the native anatomic centre of rotation of the femoral head within the acetabular shell be located and maintained during the implantation of the replacement structure. Misplacement of the centre of rotation during implantation of the femoral component of the hip joint prosthesis can affect the patient's leg length, which can lead to a very unsatisfactory result for the patient.

It is important in primary total hip arthroplasty to determine the natural offset and neck length of the femoral head by measurement. Offset can be measured from a point on the greater trochanter to the centre of the femoral head. Neck length can be measured from a point of the lesser trochanter to the centre of the femoral head.

U.S. Pat. No. 6,258,097 discloses an orthopaedic instrument for comparing post-surgical joint geometry to pre-surgical joint geometry. The instrument includes a head chuck that can be secured to the ball of a ball joint, and an arm having reference indicia thereon. Markings indicative of the pre-surgical joint geometry are made on the bone with reference to the centre of the ball joint. After replacement with a prosthetic ball, the post-operative geometry is verified by securing the head chuck to the prosthetic ball, and comparing the location of the bone markings against the reference indicia on the arm. As needed, adjustments are made in the prosthetic components.

There remains a need for surgical instruments that will assist surgeons to resect the femoral neck at the appropriate resection plane in order to reproduce within the artificial joint the hip's anatomic centre of rotation. Furthermore, the current resection guides do not take into account the variety of head offsets that can be templated and so leaves the surgical procedure open to an increase risk of error.

SUMMARY OF THE INVENTION

According to a first aspect of the invention there is provided a surgical device for performing a controlled resection of the neck of a femur during a hip replacement procedure, the surgical device comprising:

a template comprising an aperture dimensioned for mounting the template on a femoral head of the femur, and a frame comprising a resection guide for indicating a resection plane on the femoral neck, said femoral neck having a femoral neck axis, wherein said frame is slidably connected to the template for positioning of the resection guide along the femoral neck axis while the template is mounted on the femoral head.

The aperture may be dimensioned for receiving a femoral head of the femur. The aperture may be substantially oval or circular. In some constructions, the aperture may be dimensioned to receive a securing element, for example a bone pin, for securely mounting the template on an outer surface of the femoral head.

In some constructions, the frame comprises a base portion from which a single arm may extend in a proximal direction. The template is connected to the frame via the arm. For example, the arm may comprise a channel, with a portion of the template being slidably received within the channel. The portion of the template that may be slidably received within the channel may be a perimeter edge of the template.

In some constructions, the channel is an open ended slot extending from a free end of the arm along at least a part of the length of the arm in a distal direction towards the base portion. As such, the portion of the template that is received within the slot is sandwiched between an upper section of the arm and a lower section of the arm. In some constructions, the portion of the template that is received within the slot is a perimeter edge of the template.

In order to reduce inventory of surgical instruments, advantageously the surgical device of the invention is designed to be used on the right and left hip, and for a posterior approach or an anterior approach. Therefore, in some constructions the frame may include a pair of spaced apart arms, with each arm extending from the base portion in a proximal direction. The spaced apart arms may be substantially parallel. The frame may be generally U-shaped.

The template is connected to frame via the pair of arms. Again, each arm of the pair of arms may comprise a channel, with a first portion of the template being slidably received within the channel within the first arm, and a second portion of the template being slidably received within the channel within the second arm. In some constructions, the channel is an open ended slot extending in a distal direction from a free end of each arm of the pair of arms, along at least a part of the length of each arm. The portion of the template that is received within the slot is therefore sandwiched between an upper section and a lower section of the arm. In some constructions, the portion of the template that is received within the slot is a perimeter edge of the template.

The resection guide may extend distally from the base portion of the frame. The resection guide may include a first surface that indicates a resection plane for a standard offset neck. The resection guide may also include a second surface that indicates a resection plane for a high offset neck.

The resection guide may comprise a foot that extends distally from the base portion of the frame.

In order to reduce inventory of surgical instruments, advantageously the surgical device of the invention is designed to be used on the right and left hip, and for a posterior approach or an anterior approach. Therefore, in some constructions the frame includes two resection guides that are mirror images of each other. For example, the frame may include a first resection guide that comprises a first foot, and a second resection guide that comprises a second foot. Each foot may include a first surface that indicates a resection plane for a standard offset neck, and a second surface that indicates a resection plane for a high offset neck.

Prior to resecting the femoral neck, it may be advantageous for a surgeon to be able to easily establish the location of the resection plane along the femoral neck axis that will result in a distinct femoral head offset. This distinct femoral head offset may correspond to the anatomical femoral head offset. Accordingly, the surgical device according to the invention may include a slidable connection that is indexed such that resection guide can be located at plurality of discrete positions along the femoral neck axis. Each discrete position may relate to a distinct femoral head offset.

As a non-limiting example, the slidable connection may be indexed such that the resection guide can be located along the femoral neck axis at three discrete positions. Positioning of the resection guide on the femoral neck at the first discrete position will indicate to the surgeon the location of a resection plane that will provide a first femoral head offset. Positioning of the resection guide on the femoral neck at the second discrete position will indicate to the surgeon the location of a resection plane that will provide a second femoral head offset, this being different to the first femoral head offset. Positioning of the resection guide on the femoral neck at the third discrete position will indicate to the surgeon the location of a resection plane that will provide a third femoral head offset, this being different from both the first and second femoral head offsets.

As the resection guide is moved more medially along the femoral neck axis there will be a concomitant reduction in the femoral head offset of the trial or definitive femoral head relative to the femoral shaft axis, if the surgeon resects the femoral neck along the resection plane indicated by the resection guide.

In an exemplary hip implant system, the first femoral head offset may be −2 mm, the second femoral head offset may be +5 mm, and the third femoral head offset may be +12 mm.

The indexing of the slidable connection between the template and the frame may comprise a plurality of calibration elements. Each calibration element corresponds to a distinct femoral head offset. The plurality of calibration elements may be arranged along the length of the arm or at least one arm of the pair of arms. The single head offset selector may be provided on the template. Positioning of the single femoral head offset selector relative to one of the plurality of calibration elements locates the resection guide at a discrete position along the femoral axis. This discrete position defines a resection plane that corresponds to the selected distinct femoral head offset.

It is envisaged that in some constructions of the surgical device, the plurality of calibration elements provided on the arm or at least on one arm of the pair of arms may comprise markings or indicia. These markings or indicia may be etched into or laser marked onto the surface of the arm. The single head offset selector provided on the template may also comprise a single marking or indicium. It is envisaged that this marking or indicia may be etched into, laser marked onto, mechanically engraved into, or moulded into the surface of the template.

Each arm has a longitudinal axis extending along its length. The markings or indicia on the arm or on at least one arm of the pair of arms may comprise a set of lines arranged along the length of the arm, with each line extending perpendicular to the longitudinal axis of the arm. The spacing between each line and the resection guide is calibrated so as to locate the resection guide along the femoral neck axis at a discrete position that indicates a resection plane corresponding to a distinct femoral head offset.

The single marking on the template may be a line.

The surgeon may slide the template relative to the frame until the single line on the template is aligned with a chosen line on the arm. This will locate the resection guide at a discrete position along the femoral neck axis that defines a resection plane corresponding to a distinct femoral head offset.

It is envisaged that in alternative constructions of the device, each of the plurality of calibration elements provided on the frame comprises a cut-out formed within the upper surface of the arm or at least one arm of the pair of arms. The plurality of cut-outs are spaced along the length of the arm.

In a specific construction of the device, each cut-out extends from an internally located edge of the or each arm. The cut-out is substantially semi-circular. Visually the upper surface of the channel is scalloped. The single projection on the template is substantially semi-circular.

The spacing between each cut-out and the resection guide is calibrated so as to locate the resection guide along the femoral neck axis at a discrete position that indicates a resection plane corresponding to a distinct femoral head offset.

In this construction, the single femoral head offset selector provided on the template comprises a single projection configured for alignment with any one of said plurality of cut-outs.

The surgeon may slide the template relative to the frame until the single semi-circular projection is aligned with a chosen cut-out. This will locate the resection guide at a discrete position along the femoral neck axis that defines a resection plane corresponding to a distinct femoral head offset.

It is also envisaged that in alternative constructions of the device, each of the plurality of calibration elements provided on the arm comprises an arm aperture formed within the upper surface of at least one arm. The plurality of arm apertures are spaced along the length of the arm.

The spacing between each arm aperture and the resection guide is calibrated so as to locate the resection guide along the femoral neck axis at a discrete position that indicates a resection plane corresponding to a distinct femoral head offset.

The single femoral head offset selector provided on the template comprises a single template aperture configured for alignment with any one of the plurality of arm apertures.

The surgeon may slide the template along the channel until the single template aperture is aligned with a chosen arm aperture. This will locate the resection guide at a discrete position along the femoral neck axis that defines a resection plane corresponding to a distinct femoral head offset.

It is envisaged that a locking element may be used to lock the template relative to the frame. This locking element may comprise a dowel. Accordingly, each one of the plurality of arm apertures, and the single template aperture are dimensioned to removably receive a dowel.

In order to reduce inventory of surgical instruments, advantageously the surgical device of the invention is designed to be used on the right and left hip, and for a posterior approach or an anterior approach. Accordingly a first plurality of calibration elements may be provided on an upper surface of the first arm, and a second plurality of calibration elements may be provided on a lower surface of the second arm. The first plurality of calibration elements may be duplicated by the second plurality of calibration elements. This means that the device can simply be flipped over, allowing the same device to be used regardless of which hip is being operated on, or which surgical approach is being used.

In an exemplary device, the first plurality of calibration elements may comprise a first calibration element that corresponds to a −2 mm femoral head offset, a second calibration element that corresponds to a +5 mm femoral head offset, and a third calibration element that corresponds to a +12 mm femoral head offset. Likewise, the second plurality of calibration elements may comprise a fourth calibration element that corresponds to a −2 mm femoral head offset, a fifth calibration element that corresponds to a +5 mm femoral calibration head offset, and a sixth calibration element that corresponds to a +12 mm femoral head offset.

In another construction, the first plurality of calibration elements and the second plurality of calibration elements are not duplicates.

In an exemplary device, the first plurality of calibration elements may correspond to a −2 mm, +5 mm, and +8 mm femoral head offset, and the second plurality of calibration elements may correspond to a +12 mm, +15 mm, and +17.5 mm femoral head offset. This means that when a surgeon flips the device over, s/he is presented with a different range of distinct femoral head offsets.

In a further alternative construction of the device, the indexable slidable connection between the template and the frame is achieved via a threaded connection, for example a thumbwheel connection. As a skilled artisan will understand, a thumbwheel is a control mechanism that consist of a partially exposed wheel that can be turned by moving the exposed edge with a thumb or finger.

It is envisaged that in any of the constructions of the femoral neck resection guide as described herein, a straight edge or a marked straight line may be provided on at least one of the template or the frame. This straight edge or marked straight line may be used to indicate the location of the femoral neck axis.

According to a second aspect of the invention there is provided a kit for use in orthopaedic surgery, comprising:

a first surgical device as described herein, wherein the plurality of calibration elements correspond to a first set of distinct femoral head offsets, and a second surgical device as described herein, wherein the plurality of calibration elements correspond to a second set of distinct femoral head offsets.

According to a third aspect of the invention there is provided a method of performing a controlled resection of a femoral neck comprising the steps of:

using a surgical device according to the first aspect of the invention, mounting the template on a femoral head; and positioning the resection guide along the femoral neck axis at a discrete resection plane that corresponds to a distinct femoral head offset.

The step of positioning the resection guide along the femoral neck axis at a discrete resection plane may comprise the step of the surgeon aligning a single head offset selector provided the template with one of a plurality of calibration elements arranged along the length of the arm or at least one arm of the pair of arms, wherein each calibration element corresponds to distinct femoral head offset.

Although particular constructions of this disclosure have been described, it will be appreciated that many modifications/additions and/or substitutions may be made within the scope of the claims.

BRIEF DESCRIPTION OF THE DRAWINGS

Constructions of this disclosure will be described hereinafter, by way of example only, with reference to the accompanying drawings in which like reference signs relate to like elements and in which.

DETAILED DESCRIPTION

Constructions of this disclosure are described in the following with reference to the accompanying drawings.

Figure 1:
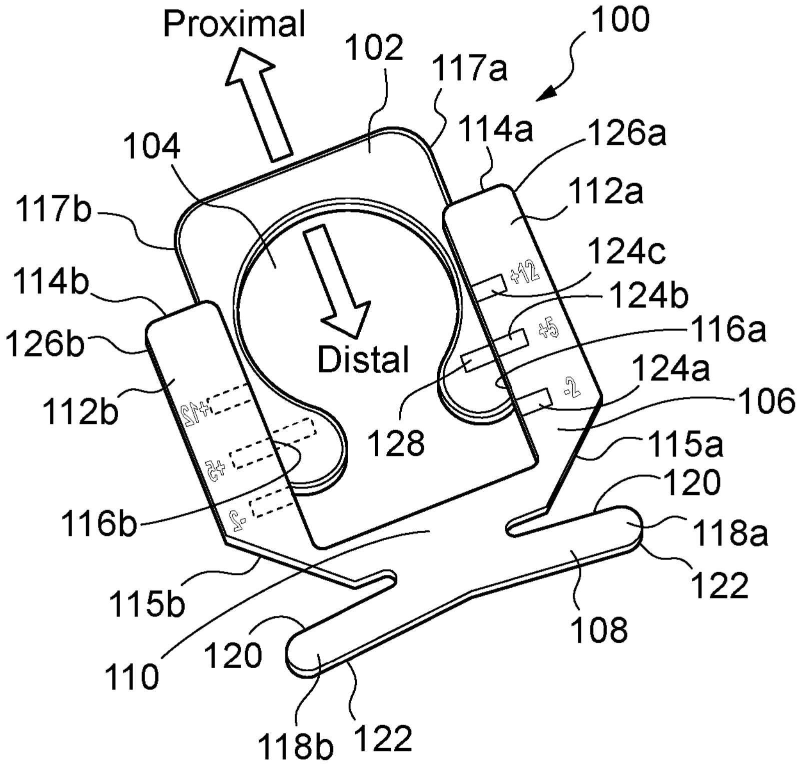
FIG. 1 shows a schematic of a first construction of the surgical device according to the first aspect of the invention.

A first construction of the device 100 is shown in FIG. 1. The device includes a template 102 comprising an aperture 104 dimensioned for receiving a femoral head of the femur and a frame 106 comprising a resection guide 108 for indicating a resection plane on along the femoral neck axis of a femoral neck.

The aperture 104 is substantially circular.

Figure 2:
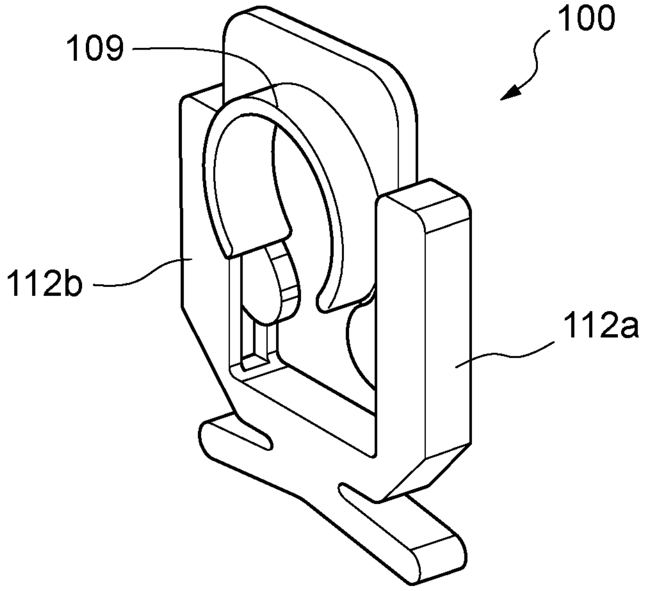
FIG. 2 shows a perspective view of the device of FIG. 1.

As shown in FIG. 2, the template 102 may also include a projecting rim or collar 109 which extends at least partially about the perimeter of the aperture 104. The projecting rim or collar facilitates location of the aperture onto the femur.

The projecting rim or collar shown in FIG. 2 is semi-circular and extends about a proximally-located region of the aperture. It is envisaged that the projecting rim or collar 109 may be provided on one of both surfaces of the template.

The frame includes a base portion 110 from which a pair of spaced apart arms 112*a*, 112*b* extend in a proximal direction. Each arm has a free proximal end 114*a*, 114*b*. The pair of arms and base portion form a generally U-shaped frame.

In the construction shown, a distally located edge of the arms 112*a*, 112*b* is defined by a straight edge 115*a*, 115*b*. Each straight edge 115*a*, 115*b* is angled in relation to the longitudinal axis of each arm. Each straight edge 115*a*, 115*b* can be used to indicated the location of the femoral axis.

A channel (not shown) is formed in each arm and is open along the internal edge 116*a*, 116*b* of each arm. The slot is dimensioned for slidable receipt of the template. In this construction, an opposing perimeter edge 117*a*, 117*b* of the template is slidably received within the slot.

The resection guide 108 extends distally from the base portion 110 of the frame. In this construction, the resection guide comprises a first foot 118*a* and a second foot 118*b*, with each foot being a mirror image of the other foot. Each foot has a first resection surface 120 that corresponds to a standard offset resection plane, and a second (more distally placed) resection surface 122 that corresponds to a high offset resection plane.

The slidable connection between the template and the frame is indexed. In this construction, the arm 112*a* includes a plurality of calibration elements spaced provided along its length. Each calibration element 124 is defined by a laser marking in the form of a horizontally oriented line. Each horizontal line extends from the internal edge 116*a*, 116*b* approximately half-way to the external edge 126*a*, 126*b* of each arm.

In the construction shown in FIG. 1, there are three calibration elements 124*a-c*. Adjacent to each calibration element is secondary indicia: "−2", "+5" and "+12".

The calibration elements/secondary indicia shown on this first construction of the surgical device relate to an exemplary hip system, in which the most distally placed calibration element 124*a* corresponds to a −2 mm femoral head offset; the centrally placed calibration element 124*b* corresponds to a +5 mm femoral head offset, and the most proximally placed calibration element 124*c* corresponds to a +12 mm femoral head offset.

A single femoral head offset selector 128 is provided on the template. In this construction, the single femoral head offset selector 128 is defined by a laser marking in the form of a horizontal line, identical in design to the calibration elements 124*a-c*.

In use, when a surgeon has mounted the device 100 on a femoral head (not shown), s/he is able to slide the frame in a distal direction relative to the mounted template in order to place the resection guide 108 in one of three different positions along the femoral neck axis (not shown). The positioning of the resection guide 108 depends on which line of the plurality of lines 124*a-c* (i.e., the calibration elements) the surgeon chooses to align the single line 126 (i.e., the femoral head offset selector) with.

In the construction shown in FIG. 1, the single femoral head offset selector 128 is shown aligned with calibration element 124*b*. Accordingly, this will locate the resection guide 108 along the femoral neck axis in a position that establishes a femoral neck resection plane corresponding to a +5 mm femoral head offset.

It is envisaged that the calibration elements 124*a-c* are duplicated on the underside of arm 112*b*. These are shown as ghost dotted lines in FIG. 1. It is also envisaged that the single femoral head offset selector 128 is duplicated on the underside of the template. This is also shown as a ghost dotted line in FIG. 1. This means that the surgical device 100 can simply be flipped over for use on a different hip or within a different surgical approach, and the surgeon is provided with the same information.

Turning to FIG. 2, the second construction of the device 200 is similar in design to the first construction 100 of the device. The design differs in the indexing mechanism used to select the location of the resection guide on the femoral neck axis (not shown).

In this construction, each of the plurality of calibration elements 224 is defined by a semi-circular cut-out formed within the upper surface of each arm 212*a*, 212*b*. Each cut-out extends from an internally located edge 216*a*, 216*b* of the arm. Visually the upper surface of the channel is scalloped.

In the construction shown in FIG. 2, there are three calibration elements 224*a-c*. Adjacent to each calibration element is secondary indicia: "−2", "+5" and "+12".

The calibration elements/secondary indicia shown on this second construction of the surgical device relate to an exemplary hip system, in which the most distally placed calibration element 224*a* corresponds to a −2 mm femoral head offset; the centrally placed calibration element 224*b* corresponds to a +5 mm femoral head offset, and the most proximally placed calibration element 224*c* corresponds to a +12 mm femoral head offset.

In this construction, the single femoral head offset selector 228 provided on the template is defined by a single semi-circular projection extending from opposing perimeters edges 217*a*, 217*b* of the template.

In use, when a surgeon has mounted the device 200 on a femoral head (not shown), s/he is able to slide the frame in a distal direction relative to the mounted template in order to place the resection guide 208 in one of three different positions along the femoral neck axis (not shown). The positioning of the resection guide 208 depends on which of the semi-circular recesses 224*a-c* (i.e., the calibration elements) the surgeon chooses to align the single semi-circular projection 228 (i.e., the femoral head offset selector) with.

In the construction shown in FIG. 2, the single femoral head offset selector 228 is shown aligned with calibration element 224*b*. Accordingly, this will locate the resection guide 208 along the femoral neck axis in a position that establishes a femoral neck resection plane corresponding to a +5 mm femoral head offset.

Figure 3:
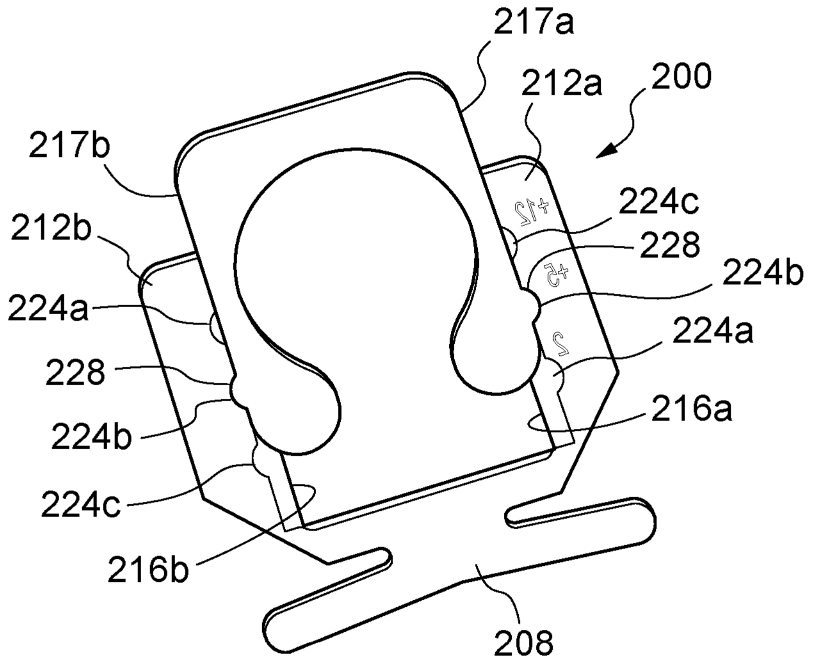
FIG. 3 shows a schematic of a second construction of the surgical device according to the first aspect of the invention.

Turning to FIG. 3, the third construction of the device 300 is similar in design to both the first construction 100, and the second construction 200 of the device. The design differs in the indexing mechanism used to select the location of the resection guide on the femoral neck axis (not shown).

In this construction, each of the plurality of calibration elements 324*a-c* is defined by a circular aperture formed within the upper surface of each arm 312*a*, 312*b*.

The calibration elements 324*a-c* provided on this third construction of the surgical device relate to an exemplary hip system, in which the most distally placed calibration element 324*a* corresponds to a −2 mm femoral head offset; the centrally placed calibration element 324*b* corresponds to a +5 mm femoral head offset, and the most proximally placed calibration element 324*c* corresponds to a +12 mm femoral head offset.

In this construction, the single femoral head offset selector 328 provided on the template is defined by a single circular aperture.

In use, when a surgeon has mounted the device 300 on a femoral head (not shown), s/he is able to slide the frame in a distal direction relative to the mounted template in order to place the resection guide 308 in one of three different positions along the femoral neck axis (not shown). The positioning of the resection guide 308 depends on which of the circular apertures 324*a-c* (i.e., the calibration elements) the surgeon chooses to align the single aperture 328 (i.e., the femoral head offset selector) with.

In the construction shown in FIG. 3, the single femoral head offset selector 328 is shown aligned with calibration element 324*c*. Accordingly, this will locate the resection guide 308 along the femoral neck axis in a position that establishes a femoral neck resection plane corresponding to a +12 mm femoral head offset.

Figure 4:
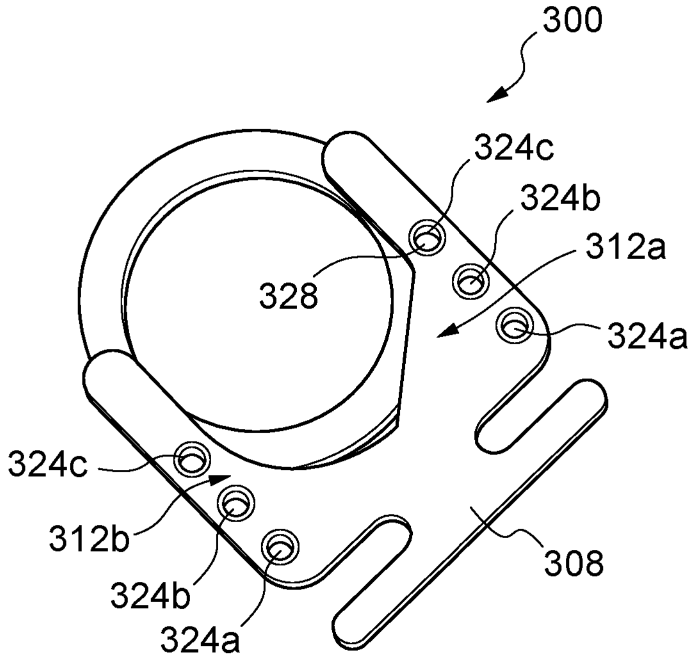
FIG. 4 shows a schematic of a third construction of the surgical device according to the first aspect of the invention.

Turning now to FIG. 4, the fourth construction of the device 400 is similar in design to both the first construction 100, the second construction 200, and the third construction 300 of the device. The design differs in the indexing mechanism used to select the location of the resection guide on the femoral neck axis (not shown). In this device the indexing mechanism comprises a thumbwheel 450 disposed on a threaded shaft 460. This allows a surgeon to slide the frame relative to the template, when the template is mounted on a femoral head.

Figure 5:
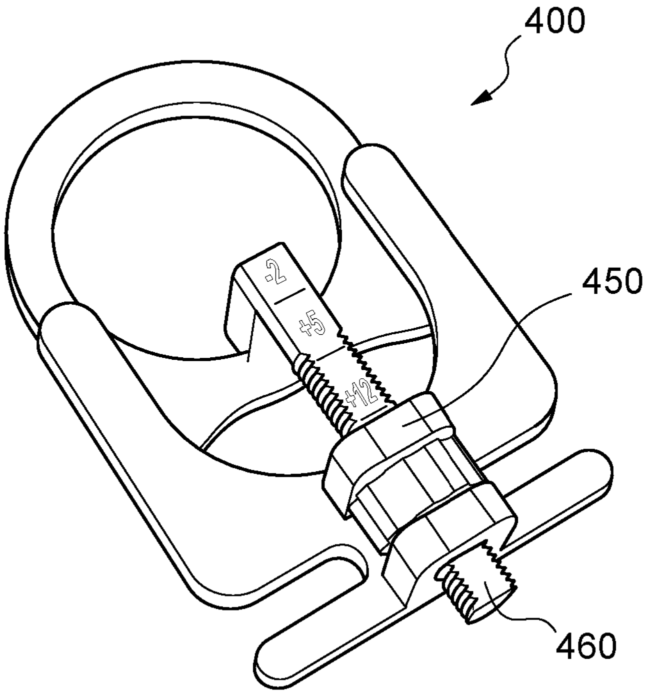
FIG. 5 shows a schematic of a fourth construction of the surgical device according to the first aspect of the invention.
Figure 6A:
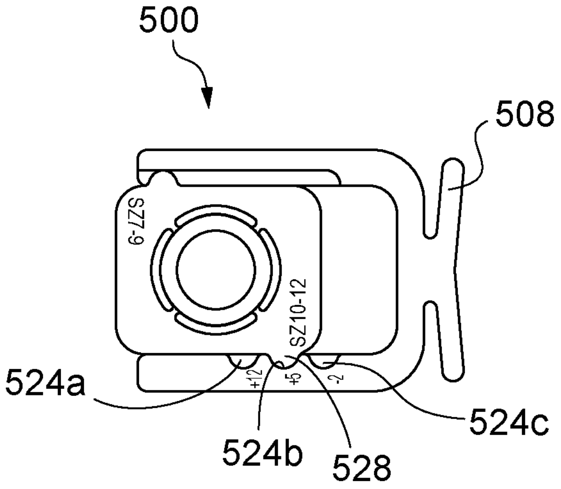
FIGS. 6A-6D show a schematic of a fifth construction of the surgical device according to the first aspect of the invention.
Figure 6B:
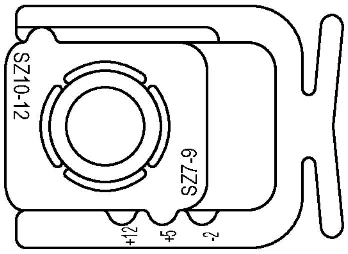
Figure 6C:
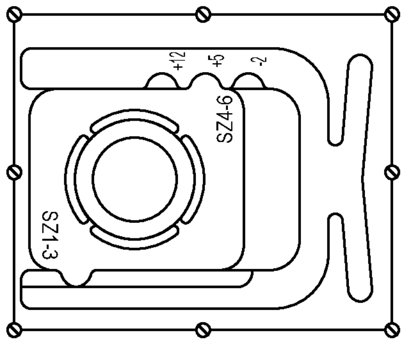
Figure 6D:
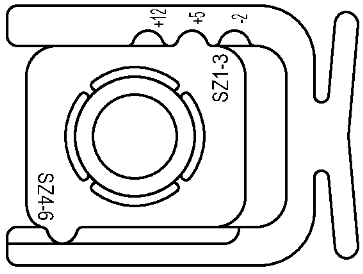

Finally, in FIG. 5 there is a so-called "4-in-1" surgical design according to the first aspect of the invention. This fifth construction 500 of the device is similar to the second construction 200 of the device. Advantageously, this design uses the same assembly of a single template and a single frame to cover a range of femoral head offsets in conjunction with range of stem sizes. This reduces the inventory.

In an exemplary hip system, the stem size ranges from size 1 to size 12, that can be subdivided into four groups:

Group A: stem sizes 1-3;
Group B: stem sizes 4-6;
Group C: stem sizes 7-9; and
Group D: stem sizes 10-12

The surgical device 500 template can be used in four different orientations, as shown in FIG. 5*a-d*, with each orientation covering one of the Groups A-D.

Positioning the semi-circular protrusion 528 (i.e., the single femoral head offset selector) in relation to one of the semi-circular cut outs 524*a-c* (i.e., the plurality of calibration elements) will position the resection guide 508 in a discrete resection plane along the femoral neck axis for a combination of a selected stem size and a selected femoral head offset. The asymmetric positioning of the semi-circular protrusions working with the asymmetric position of the semi-circular cut out allows for the ascending size and offset range to be accommodated.

As shown in FIG. 5*a*, the device 500 can be used to position the resection guide 508 in the correct place along the femoral neck axis for a stem selected from Group D with a standard femoral head offset of +5 mm.

By rotating the template about 180°, as shown in FIG. 5*b*, the same device 500 can be used to position the resection guide 508 in the correct place along the femoral neck axis for a stem selected from Group C with a standard femoral head offset of +5 mm.

If the template is flipped over, as shown in FIG. 5*c*, the same device 500 can be used to position the resection guide 508 in the correct place along the femoral neck axis for a stem selected from Group B with a standard femoral head offset of +5 mm.

By rotating the template about 180°, as shown in FIG. 5*d*, the same device 500 can be used to position the resection guide 508 in the correct place along the femoral neck axis for a stem selected from Group A with a standard femoral head offset of +5 mm.

Figure 7A:
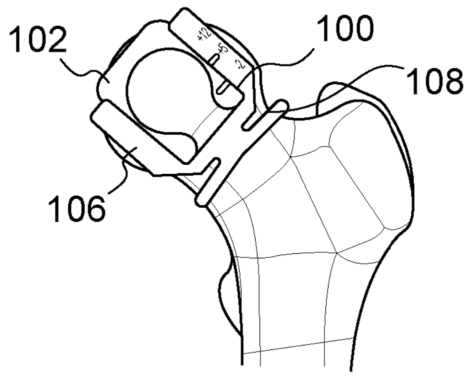
FIGS. 7A-7C show the first construction of the device being transitioned between different femoral head offset positions.
Figure 7B:
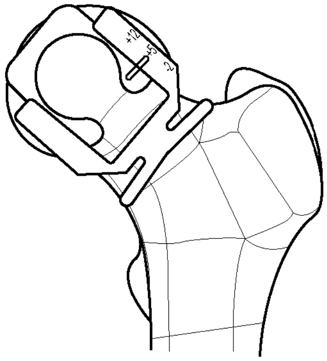
Figure 7C:
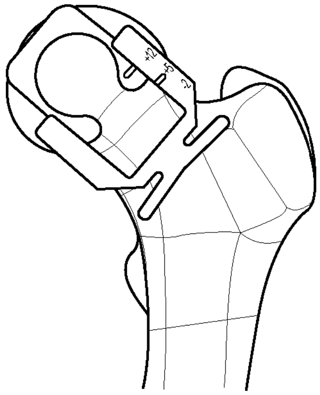

FIG. 7 shows the transition of the first construction of the device 100 between different femoral head offsets, and shows the relative positioning of the resection guide 108 on the femoral neck. A surgeon can slide the template 102 within the frame 106 between the −2 mm position (FIG. 7*a*), the +5 mm position (FIG. 7*b*), and the +12 mm position (FIG. 7*c*).

The invention claimed is:

1. A surgical device for performing a controlled resection of a neck of a femur during a hip replacement procedure, the surgical device comprising:

a template having an upper surface and an opposite lower surface, the template comprising a proximal base portion, a pair of template arms that extend distally from the proximal base portion, circular-shaped aperture extending from the template's upper surface to the template's lower surface and defined between the pair of template arms and dimensioned for mounting the template to a femoral head of the femur, and a circular-shaped projecting rim projecting away from the template's lower surface and extending at least partially about a perimeter of the aperture, and a frame having an upper surface and an opposite lower surface, the frame comprising a distal base portion, a pair of frame arms that extend proximally from the distal base portion, wherein the distal base portion and the pair of frame arms form a U-shaped frame such that proximal ends of the pair of frame arms are spaced apart from each other to define an opened proximal end of the frame, and a resection guide configured to indicate a resection plane on the femoral neck, said femoral neck having a femoral neck axis, the resection guide comprising a first foot and a second foot with each of the first foot and the second foot having a first resection surface corresponding to a standard offset resection plane and a second resection surface corresponding to a high offset resection plane, each of the first resection surfaces being closer to the proximal end of a respective one of the pair of frame arms than the second resection surfaces, wherein the upper and lower surfaces of the template and the upper and lower surfaces of the frame are all substantially parallel with one another, wherein each of the pair of template arm includes a perimeter edge that is slidably received within a channel of a corresponding frame arm of the pair of frame arms such that the frame is slidably connected to the template for moving the resection guide linearly toward and away from the circular-shaped aperture of the template and positioning of the resection guide along the femoral neck axis while the template is mounted on the femoral head.

2. The surgical device of claim 1, wherein the pair of frame arms are substantially parallel.

3. The surgical device of claim 1, wherein each frame arm of the pair of frame arms includes an internal edge in which the channel of the respective frame arm is defined.

4. The surgical device of claim 1, wherein the resection guide extends distally from the distal base portion of the frame.

5. The surgical device of claim 1, wherein the slidable connection is indexed such that the resection guide can be located at a plurality of discrete positions along the femoral neck axis.

6. The surgical device of claim 5, wherein a plurality of calibration elements corresponding to distinct femoral head offsets are arranged along a length of at least one frame arm of the pair of frame arms, and wherein a single femoral head offset selector is provided on the template, such that positioning of the single femoral head offset selector relative to one of the plurality of calibration elements locates the resection guide at one of the plurality of discrete positions along the femoral neck axis, said one of the plurality of discrete positions defining a resection plane corresponding to the respective distinct femoral head offset.

7. The surgical device of claim 6, wherein the plurality of calibration elements on the at least one frame arm of the pair of frame arms comprises a set of markings, and the single femoral head offset selector on the template comprises a single marking.

8. The surgical device of claim 7, wherein the set of markings on the at least one frame arm of the pair of frame arms comprises a set of spaced apart lines, and the single marking on the template is a line.

9. The surgical device of claim 6, wherein each of the plurality of calibration elements provided on the at least one frame arm comprises a cut-out, and wherein the single femoral head offset selector comprises a single projection configured for alignment with each cutout.

10. A kit for use in orthopaedic surgery, comprising:

a first surgical device of claim 6, wherein the plurality of calibration elements correspond to a first set of distinct femoral head offsets, and a second surgical device of claim 6, wherein the plurality of calibration elements correspond to a second set of distinct femoral head offsets.

11. The surgical device of claim 1, wherein the distal base portion and the pair of frame arms of the frame enclose the aperture defined between the pair of template arms of the template.

* * * * *